(12) United States Patent
Czupalla et al.

(10) Patent No.: US 11,278,191 B2
(45) Date of Patent: Mar. 22, 2022

(54) OPTICAL MEDICAL INSTRUMENT

(71) Applicant: Karl Storz SE & Co. KG, Tuttlingen (DE)

(72) Inventors: Christian Czupalla, Tuttlingen (DE); Peter Eisenkolb, Tuttlingen (DE); Andreas Heni, Tuttlingen (DE); Markus Kupferschmid, Tuttlingen (DE)

(73) Assignee: Karl Storz SE & Co. KG, Tuttlingen (DE)

(*) Notice: Subject to any disclaimer, the term of this patent is extended or adjusted under 35 U.S.C. 154(b) by 319 days.

(21) Appl. No.: 15/332,554

(22) Filed: Oct. 24, 2016

(65) Prior Publication Data

US 2017/0112369 A1 Apr. 27, 2017

(30) Foreign Application Priority Data

Oct. 26, 2015 (DE) .......................... 102015118199.1

(51) Int. Cl.
*H04N 13/239* (2018.01)
*A61B 1/00* (2006.01)
(Continued)

(52) U.S. Cl.
CPC .......... *A61B 1/00193* (2013.01); *A61B 1/042* (2013.01); *A61B 1/055* (2013.01);
(Continued)

(58) Field of Classification Search
CPC ..... A61B 1/00193; A61B 1/042; A61B 1/055; A61B 1/00; G02B 23/2415; G02B 23/2446; G02B 23/2453; G02B 23/2469; G02B 23/2484; G02B 23/2476; G02B 23/2423; H04N 13/0239; H04N 13/0296; H04N 2005/2255; H04N 7/18; H04N 13/239

See application file for complete search history.

(56) References Cited

U.S. PATENT DOCUMENTS 5,166,787 A * 11/1992 Irion ................. A61B 1/00181
  348/75
5,575,757 A * 11/1996 Kennedy ............ A61B 1/00188
  348/65

(Continued)

FOREIGN PATENT DOCUMENTS

DE 102004023866 B3 2/2006
DE  60302574 T2 6/2006
(Continued)

OTHER PUBLICATIONS

German Search Report Application No. 10 2015 118 199.1 Completed: Aug. 3, 2016 dated Aug. 8, 2016 8 Pages.

*Primary Examiner* — Patrick E Demosky
(74) *Attorney, Agent, or Firm* — Whitmyer IP Group LLC (57) ABSTRACT

An optical instrument for capturing stereo images includes two optical devices for producing a real image in each case, two carriages, which are each movable along a predetermined path relative to one of the optical devices, two image sensors, each with a light-sensitive surface for capturing the respective real image, with one of the image sensors in each case being fastened to the carriage, and one reflecting surface in the beam path between the optical device and the image sensor in each case.

20 Claims, 3 Drawing Sheets

(51) Int. Cl.
  *H04N 13/296* (2018.01)
  *A61B 1/04* (2006.01)
  *A61B 1/055* (2006.01)
  *G02B 23/24* (2006.01)
  *H04N 5/225* (2006.01)

(52) U.S. Cl.
  CPC ..... *G02B 23/2415* (2013.01); *G02B 23/2446* (2013.01); *G02B 23/2453* (2013.01); *G02B 23/2469* (2013.01); *G02B 23/2484* (2013.01); *H04N 13/296* (2018.05); *H04N 2005/2255* (2013.01)

(56) References Cited

U.S. PATENT DOCUMENTS

| | | | |
|---|---|---|---|
| 5,588,948 A | | 12/1996 | Takahashi et al. |
| 6,117,071 A | * | 9/2000 | Ito ............... A61B 1/00059 600/118 |
| 9,192,286 B2 | * | 11/2015 | Kazakevich ......... A61B 1/0005 |
| 2004/0189799 A1 | * | 9/2004 | Spencer ............ A61B 1/00188 348/85 |
| 2007/0100209 A1 | | 5/2007 | Takahashi |
| 2013/0162776 A1 | * | 6/2013 | Noack ............... A61B 1/0008 348/45 |
| 2014/0210945 A1 | * | 7/2014 | Morizumi .......... A61B 1/00096 348/45 |
| 2014/0343358 A1 | * | 11/2014 | Hameed ............. A61B 1/053 600/109 |
| 2016/0286197 A1 | * | 9/2016 | Schwarz ........... A61B 1/00096 |
| 2017/0095142 A1 | * | 4/2017 | McDowall ......... A61B 1/00096 |
| 2017/0112369 A1 | * | 4/2017 | Czupalla ........... G02B 23/2484 |

FOREIGN PATENT DOCUMENTS

| | | |
|---|---|---|
| DE | 102007009292 A1 | 8/2008 |
| DE | 102014103169 A1 | 9/2015 |
| EP | 0841586 B1 | 5/1998 |
| EP | 1514150 B1 | 3/2005 |
| EP | 2162050 B1 | 3/2010 |
| WO | 2014012103 A1 | 1/2014 |

* cited by examiner

OPTICAL MEDICAL INSTRUMENT

TECHNICAL FIELD

The present invention relates to an optical medical instrument or another optical instrument, in particular to an endoscope, an exoscope or an operating microscope, in which an image sensor is movable or displaceable, or two image sensors are movable or displaceable independently of one another, for compensating imaging aberrations and/or for focusing in the case of a varying object distance.

BACKGROUND

For a long time, every medical endoscope had an eyepiece which facilitated a direct view through the endoscope. Cameras were developed later; these could be mechanically connected and optically coupled to the eyepiece of an endoscope in order to facilitate a reproduction of the image captured by the endoscope on a large screen and optionally to facilitate the storage thereof. Furthermore, this modularity facilitates autoclaving of the endoscope without consideration for the separate camera and combining the same camera with different endoscopes.

A flexible endoscope often has a coherent bundle of optical fibers and can be coupled to a camera, just like a rigid endoscope. Alternatively, an image sensor is arranged at the distal end of the flexible endoscope. US 2007/0100209 A1 describes an endoscope with an image sensor at the distal end. A shape memory element is provided for moving a movable lens or the image sensor in the direction parallel to the optical axis of the lens.

Stereoscopic endoscopes are described in U.S. Pat. No. 5,588,948, EP 0 841 586 B1 and in WO 2014/012103 A1.

EP1514150B1 has disclosed an endoscope for simultaneous video and direct observation, comprising an image sensor and a beam splitter. Image sensor, beam splitter and eyepiece lens are arranged on a movable component which may be displaced parallel to the beam path of the direct observation by actuating a focal rim for focusing purposes. The image sensor is applied laterally to the beam splitter on a bearing column in such a way that the instrument must provide additional installation space for the sensor.

In the case of stereoscopic endoscopes with two image sensors, the adjustment of image sensors is particularly important also in view of the very small cross-sections of the observation beam paths. At the same time, conventional concepts are not transferable, or only transferable with restrictions, to stereoscopic endoscopes due to the small available installation space and the desired autoclavability.

SUMMARY

An object of the present invention consists of creating an improved optical instrument and an improved method for adjusting an image sensor of an optical instrument.

This object is achieved by the subject matter of the independent claims.

Developments are specified in the dependent claims.

Embodiments of the present invention are based on the concept of fastening an image sensor to a carriage movable along a predetermined path in a stereoscopic endoscope or in another optical instrument in order to facilitate focusing and/or correcting an optical aberration of an optical device. Here, in particular, the light emanating from the optical device is deflected by 90 degrees by means of a reflecting surface in order to facilitate focusing of the image with a movement of the image sensor parallel to the optical axis of the optical device.

An optical instrument comprises an optical device for producing a real image, a carriage which is movable relative to the optical device along a predetermined path and lockable or locked, and an image sensor with a light-sensitive surface for capturing the real image, with the image sensor being fastened to the carriage.

An optical instrument comprises two optical devices for producing two real images, two carriages, which are movable independently of one another relative to the optical devices, in each case along a predetermined path, and which are optionally lockable or locked, and two image sensors, each with a light-sensitive surface for capturing respectively one of the two real images, with one of the two image sensors being fastened to each one of the two carriages.

An optical system for capturing stereo images comprises two optical devices for producing a real image in each case, two carriages arranged at or near the proximal end of the optical instrument, said carriages each being movable along a predetermined path relative to the optical devices and lockable, two image sensors, each with a light-sensitive surface for capturing the respective real image, with one of the image sensors in each case being fastened to the carriage, and one reflecting surface in the beam path between the optical device and the image sensor in each case.

An optical instrument comprises an optical device for producing a real image, a carriage arranged at or near the proximal end of the optical instrument, said carriage being movable along a predetermined path relative to the optical device, and lockable or locked, an image sensor with a light-sensitive surface for capturing the real image, with the image sensor being fastened to the carriage, and a reflecting surface in the beam path between the optical device and the image sensor.

In particular, the optical instrument is an optical medical instrument. In particular, the optical instrument is an endoscope, an exoscope or an operating microscope. Similar to an operating microscope, an exoscope is an instrument used in medical engineering for observing a human body, there, in particular, an operating site or the body interior, from outside the body. By way of example, such exoscopes are known from EP2162050B1. In particular, the optical instrument is a stereoscopic optical instrument for capturing two images through two entrance pupils lying next to one another, said entrance pupils facilitating a spatial perception in the case of a suitable reproduction.

In particular, the optical device comprises an objective or one or more lenses for producing the real image. The optical device may be arranged behind a relay lens system (e.g. a rod lens system according to H.H. Hopkins) or comprise such a relay lens system. Specifications in relation to the arrangement of one optical device in front of or behind another optical device in this case always relate to the propagation direction of light which emanates from an object to be observed. Arranged behind a relay lens system, the optical device is, in particular, provided and embodied for the magnifying production of a real image. Thus, in particular, the image to be captured by means of the image sensor is larger than the last real image produced by the relay lens system (which is a real intermediate image in relation to the whole optical instrument). In particular, an optical instrument for capturing stereo images comprises two relay lens systems, or else two objectives.

If the optical instrument—e.g. an—endoscope comprises a shaft and a handling device at the proximal end of the shaft, the carriage is, in particular, arranged at the proximal end of the optical instrument if it is arranged in the handling device. In other cases, the carriage is, in particular, arranged at or near the proximal end of the optical instrument when the distance of the center of gravity of the carriage from the proximal end of the optical instrument is not greater than the distance thereof (or half of the distance thereof or a third of the distance thereof or a fifth of the distance thereof or a seventh of the distance thereof) from the distal end of the optical instrument.

The carriage may be lockable or locked. If the carriage is locked, the movability of the carriage then means the movability of the carriage when the lock is lifted.

In particular, the carriage is guided in such a way that it is only movable or displaceable in one direction, i.e. only along a single straight-lined path with a predetermined length. In particular, the carriage is guided with so little play and friction that it is not, or not substantially, swivelable or tiltable. The carriage is not substantially swivelable or tiltable if it is only swivelable or tiltable within an angular range, within which such a movement has no substantial influence on the sharpness of the image captured by means of the image sensor. In particular, this is the case when each point of the light-sensitive surface of the image sensor is, at most, moved in a direction orthogonal to the light-sensitive surface along a path which is less or substantially less than the depth of field.

In particular, the carriage is only movable in a direction parallel to the longitudinal axis of the optical instrument. If the optical instrument is an endoscope with a rigid and straight shaft, the carriage is, in particular, movable parallel to the longitudinal axis of the shaft.

As described above, in particular two carriages are movable independently of one another, also counter to one another, and lockable or locked in the case of an optical instrument for capturing stereo images. In particular, the carriages can be locked at different positions.

The carriage may be formed by a circuit board or printed circuit board (PCB) made out of fiber-reinforced plastic or another material, on or in which lines or electrically conductive paths are provided. Alternatively, the carriage may be formed from metal, ceramic, plastic or any other electrically conductive or electrically insulating material, without comprising lines or other electrically conductive paths, or being part of a circuit, at the same time. A configuration of the carriage without the function of a printed circuit board e.g. made of metal, ceramic or a suitable plastic may facilitate particularly precise manufacturing of the carriage and guidance of the carriage with particularly little play and friction.

In particular, the image sensor is provided, embodied and arranged to directly capture the real image produced by the optical device. Thus, no further imaging device is provided between the optical device and the image sensor. The image sensor is provided and embodied to produce an in particular electrical signal which represents the real image.

The image sensor may be fastened directly or indirectly (e.g. by way of a printed circuit board) to the carriage. In particular, the image sensor is fastened to the carriage by adhesive bonding, a solder connection and/or in another cohesive, interlocking and/or force fit or frictional manner. If the optical instrument is an endoscope, the image sensor with carriage is arranged, in particular, in a handling device at the proximal end of the endoscope.

In particular, the reflecting surface reflects independently, or substantially independently, of the wavelength within the wavelength range to be captured by the image sensor. Thus, in particular, the reflecting surface is provided, embodied and arranged to deflect all of the light (both in terms of the cross-section and the wavelength). In particular, the reflecting surface is provided and arranged to deflect the beam path by 90 degrees. In particular, the reflecting surface is plane, i.e. it has no refractive power and does not change the object distance. In particular, the reflecting surface is provided in or on a deflection prism.

The arrangement of the image sensor on a carriage may facilitate a simple adjustment of the image sensor and a simple compensation of imaging aberrations (in particular focal distance aberrations) of the optical device and/or of a relay lens system or other optical devices through which light, which is subsequently incident on the image sensor, propagates. Alternatively, or additionally, the arrangement of the image sensor on a carriage may facilitate simple focusing in the case of a varying object distance. A deflection of the beam path by a reflecting surface in particular through 90 degrees may contribute to a particularly compact and robust structure.

By arranging the image sensors on the carriage, the sensors may be adjusted particularly easily and independently of one another in an optical instrument for capturing stereo images. Optical imaging aberrations produced by tolerances in the two stereo channels, for example in two objectives or two relay lens systems, may therefore be corrected independently of one another. In this way, it is possible to produce a virtually aberration-free stereoscopic image.

In an optical instrument as described here, the reflecting surface is, in particular, rigidly connected to the image sensor and movable together with said image sensor.

In particular, the reflecting surface is provided on or in a prism which is adhesively bonded to the light-sensitive surface of the image sensor or connected to the image sensor in a mechanically rigid manner by other means. The image sensor and the reflecting surface thus form a rigid mechanical unit, which is mechanically robust and facilitates simple handling. At the same time, the mechanically sensitive light-sensitive surface of the image sensor is protected.

In an optical instrument as described here, the carriage is movable, in particular in a direction parallel to the light-sensitive surface of the image sensor.

Movability or displaceability of the carriage in one direction (particularly exclusively in one direction) parallel to the light-sensitive surface of the image sensor is obtainable, for example, by a substantially plate-shaped configuration of the carriage, which requires little installation space and, at the same time, may be particularly mechanically rigid and robust.

In an optical instrument as described here, the light-sensitive surface of the image sensor is arranged, in particular, parallel to the optical axis of the optical device.

The optical device refers, in particular, to the optical axis of the optical device at the light-exit surface thereof. A deflection of the light emanating from the optical device by means of a reflecting surface, or in any other way, by 90 degrees may facilitate the arrangement of the light-sensitive surface of the image sensor parallel to the optical axis of the optical device.

In an optical instrument as described here, the optical axis of the beam path between the optical device and the reflecting surface is, in particular, parallel to the light-sensitive surface of the image sensor.

An optical instrument, as described here, further comprises, in particular, a clamping device for locking the carriage in a force-fit manner.

The clamping device for force fit or frictional locking of the carriage is, in particular, provided and embodied to detachably lock the carriage at any position within a predetermined range. In particular, the clamping device is embodied in such a way that the normal force produced by the clamping device during the envisaged use produces a frictional force which is greater than the forces on the carriage, occurring when using the optical instrument as intended, in the direction parallel to the direction in which said carriage is movable.

In particular, the clamping device comprises a headless screw or any other screw which, in the carriage, engages in a thread with a diameter that decreases in one direction or in a thread in a bore with a diameter that decreases in one direction. In the region of the thread or the bore with the thread, the carriage has, in particular, a slit which facilitates a deformation of the carriage by the thread being widened by the screw.

In particular, the clamping device is arranged near a straight edge portion or in a bead-shaped thickening at a straight edge portion, which is parallel to the predetermined movement direction of the carriage.

In an optical instrument for capturing stereo images, provision is made, in particular, of two clamping devices which facilitate an above-described locking of the carriages independently of one another.

An optical instrument as described here further comprises in particular a spring or another elastic device for displacing the carriage in a predetermined direction.

In particular, the predetermined direction is parallel to the optical axis of the optical device for producing a real image and/or to the longitudinal direction of the optical instrument. In particular, the spring is arranged near a straight edge portion or in a bead-shaped thickening on a straight edge-portion which is arranged parallel to the predetermined movement direction of the carriage. In particular, the spring is a compression spring which displaces the carriage in the proximal direction, with the carriage being movable in the distal direction against the elastic force of the spring manually and/or by way of a tool or by means of a tool, provided it is not locked by means of the above-described clamping device or in any other way.

Using such a spring, force needs to be exerted on to the carriage in only one direction for adjusting the optical instrument in order to move said carriage by varying the force in two opposite directions.

An optical instrument as described here further comprises, in particular, a setscrew for moving the carriage.

In particular, the setscrew is arranged near a straight edge portion or in a bead-shaped thickening at a straight edge portion which is parallel to the predetermined movement direction of the carriage. In particular, the distal end of the setscrew abuts against a wall arranged distantly in relation to the carriage.

The setscrew may facilitate a precise adjustment of the position of the carriage. The carriage can be moved or displaced in a finely metered manner in the proximal direction by rotating the setscrew in the clockwise direction; by rotating the setscrew in the counterclockwise direction and, at the same time, producing a force displacing the carriage in the distal direction, the carriage can be moved or displaced in a finely metered manner in the distal direction.

In an optical instrument for capturing stereo images, provision is made, in particular, of two setscrews, by means of which the two carriages may be adjusted independently of one another and may also be adjusted in relation to one another.

An optical instrument as described here further comprises, in particular, a drive device for moving the carriage.

The drive device comprises, in particular, a linear motor, an ultrasonic motor or a motor-driven spindle drive, which facilitates the movement of the carriage controlled by an in particular electrical control signal. Such a drive device facilitates focusing or sharpening of the image captured by means of the image sensor in the case of a varying object distance.

An optical instrument for capturing stereo images comprises, in particular, two drive devices, which facilitate the movement of the carriages independently of one another and also relative to one another.

An optical instrument as described here further comprises, in particular, a printed circuit board connected to the carriage, with the image sensor being fastened to the printed circuit board.

An optical instrument as described here further comprises, in particular, a printed circuit board connected to the carriage, with the image sensor being fastened to the printed circuit board and the printed circuit board having a flexibly curved portion facilitating a length compensation when moving the carriage.

The circuit board or printed circuit board may have one or more plies of electrically conductive conductor tracks on, or in, an electrically insulating material. The printed circuit board may be partly rigid or completely flexible, with, in particular, the part of the printed circuit board on which the image sensor is arranged being kept without movement and without deformation relative to the carriage by way of an areal adhesive connection to the carriage, or in another way.

The flexibly curved portion may be curved in such a way that it is already curved in its state of lowest mechanical stress (in particular prior to installation into the optical instrument); by way of example, it forms a double S-shaped loop. Alternatively, the flexibly curved portion may, in its state of lowest mechanical stress, have a straight or areal or substantially straight or areal design and only assume a curved design after installation into the optical instrument.

There is no need for flexible cable connections between the printed circuit board and further electrical or optical devices, which are arranged in a rigid or stationary manner within the optical instrument, in one configuration of the printed circuit board with a flexibly curved portion facilitating length compensation. Rather, a plug-in connector may be provided for example at an end of the flexibly curved portion of the printed circuit board distant from the image sensor, said plug-in connector being immediately connected to a corresponding plug-in connector at a further electrical or electronic component or a further printed circuit board within the optical instrument.

In an optical instrument for capturing stereo images, there are in particular two printed circuit boards, as described above, which may each be connected to one of the image sensors.

An optical endoscope as described here is, in particular, an endoscope with a rigid shaft. Endoscopes with electronic image sensors are also referred to as video endoscopes.

In particular, the endoscope is a medical endoscope, i.e. provided and embodied for application in medical measures. Alternatively, the endoscope may be provided and embodied for technical applications. In particular, the shaft is straight.

In an optical instrument as described here, the optical device comprises, in particular, a rod lens system or a different relay lens system.

An optical instrument as described here further comprises, in particular, a guide component which is rigidly connected to the optical device, said guide component having two grooves, in which two parallel straight edge portions, which face away from one another, of the carriage are guided.

The guide component may be rigidly connected to the optical device in an indirect or direct fashion. In particular, the guide component has the function of a sliding sleeve, in which the carriage is guided with little play and little friction. The grooves in the guide component are, in particular, two parallel grooves which face one another in the wall of a cylindrical channel in the guide component. Apart from the grooves, the cylindrical channel has e.g. a substantially circular or rectangular cross section. While the channel may, for example, be drilled or milled, the grooves, in particular, are produced by electro-erosion so as to ensure the desired geometry, which is required for guiding the carriage with little play and little friction, with high precision.

Such a guide component may simultaneously facilitate a compact and mechanically rigid and robust configuration of the optical instrument.

An optical instrument as described here is, in particular, embodied to capture stereo images and comprises two optical devices for producing a real image in each case, two image sensors for capturing a real image in each case and two carriages on which one image sensor is arranged in each case.

The optical devices each comprise, in particular, a rod lens system or another relay lens system, with the relay lens systems being arranged parallel in a shaft of the optical instrument.

Many of the properties and features of optical instruments described here are particularly advantageous, precisely in the case of an optical instrument for capturing stereo images, because they facilitate miniaturization and hence save installation space. Furthermore, an adjustment of the image sensors independently of one another by means of one carriage in each case is particularly important, precisely in the case of two optical devices for producing a real image in each case, so as to be able to correct different optical properties of the two optical devices and of relay lens systems and other optical devices arranged upstream of the optical devices, where necessary.

In particular, in an optical instrument as described here, one edge portion from each one of the two carriages is arranged, one next to the other, in each one of the two grooves.

Each one of the two grooves therefore receives two edge portions, to be precise respectively one edge portion from each one of the two carriages. Hence, the outlay for the guidance of both carriages with little play and little friction need not be doubled in relation to a situation with only one carriage.

In an optical instrument as described here, the two carriages abut, in particular, against one another in an areal manner.

Alternatively, for example, the two carriages may abut against one another only in the regions of the parallel straight edge portions thereof (which, in particular, are respectively guided together in the grooves in pairs).

In an optical instrument as described here, the two image sensors are, in particular, arranged on sides facing away from one another of the two carriages.

The two carriages with the two image sensors and, optionally, two printed circuit boards between the carriages and the image sensors are, in particular, mirror symmetrical in relation to a plane of symmetry arranged between the two carriages or rotationally symmetrical in relation to a two-fold axis of symmetry arranged between the carriages. Components made of a carriage, optionally a printed circuit board, an image sensor and, optionally, a prism or another optical component with a reflecting surface in each case may therefore have an identical embodiment and need not be distinguished according to the left-hand channel or right-hand channel.

As a result of the aforementioned measures, the components are arranged particularly compactly and in a space-saving manner such that, for example, they can be housed in the handle of a video endoscope without the latter needing to have larger dimensions than is expedient from an ergonomic point of view.

In a method for adjusting an image sensor of an optical instrument, an image of an object arranged at a predetermined position is generated and the image sensor is moved up to a position at which said image sensor captures the image in focus, wherein the image sensor is moved parallel to a light-sensitive surface of the image sensor during the step of movement.

In a method for adjusting an image sensor of an optical instrument, an image of an object arranged at a predetermined position is generated, the image sensor is moved up to a position at which said image sensor captures the image in focus and a carriage with the image sensor is locked at the position at which the image sensor captures the image in focus, wherein the image sensor is moved parallel to a light-sensitive surface of the image sensor during the step of movement.

It is already possible to establish whether the image sensor captures the image in focus prior to, or during, the step of moving the image sensor. Steps of establishing whether the image sensor captures the image in focus and of moving the image sensor may be carried out alternately repeatedly or simultaneously, until the image sensor captures the image in focus.

In particular, the carriage with the image sensor is locked by clamps.

The above-described methods for adjusting an image sensor of an optical instrument may in each case be part of a method for producing an optical instrument and may, in particular, be applied to optical instruments, as are described here, or may be applied in the case of these optical instruments.

BRIEF DESCRIPTION OF THE DRAWINGS

Below, embodiments are described in more detail on the basis of the attached figures. In detail.

DETAILED DESCRIPTION

Figure 1:
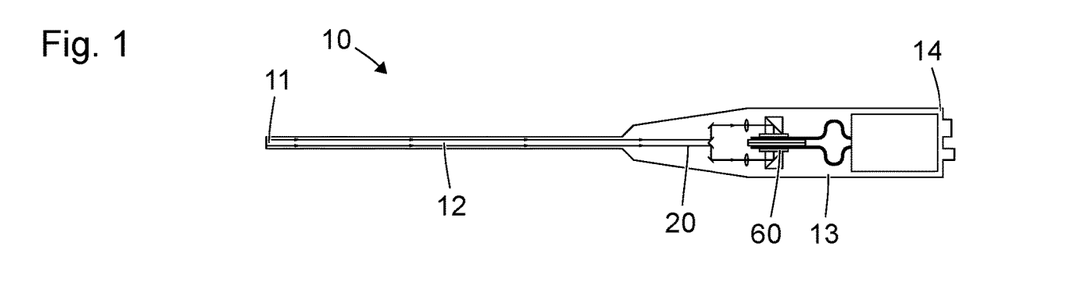
FIG. 1 shows a schematic illustration of a stereoscopic endoscope.

FIG. 1 shows a schematic illustration of a stereoscopic endoscope 10 comprising a distal end 11, a shaft 12 and a handling device 13 at the proximal end 14 of the endoscope 10. The stereoscopic endoscope has two equal observation beam paths 20, which are arranged symmetrically in relation to one another and of which only one has been provided with a reference sign in FIG. 1. The observation beam paths 20 are in each case indicated by simple lines in FIG. 1, said lines, in particular, representing the section-by-section straight optical axes of the optical elements forming the beam path. In FIG. 1, small arrows indicate the propagation direction of light along the observation beam paths 20, namely from the distal to the proximal direction or from left to right in FIG. 1, said light emanating from an object to be observed. The light transferred along the two observation beam paths 20 is captured by means of two image sensors 60 (of which only one is ever provided with a reference sign in the figures), which are likewise arranged symmetrically, and converted into (in particular electrical) signals representing two corresponding images. Spatial perception is possible in the case of a suitable reproduction of the two images.

Figure 2:
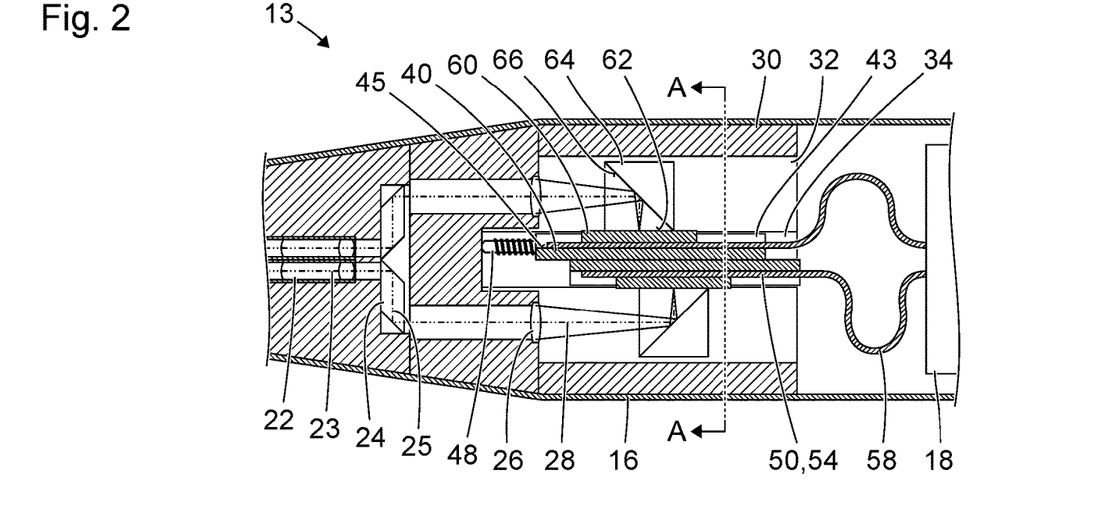
FIG. 2 shows a schematic sectional illustration of part of a stereoscopic endoscope.

FIG. 2 shows a schematic sectional illustration of part of the handling device 13 of a stereoscopic endoscope, as depicted on the basis of FIG. 1, or of part of another optical instrument. The sectional plane of FIG. 2 is parallel to the plane of the drawing of FIG. 1 and parallel to the longitudinal axis of the stereoscopic endoscope and contains the optical axes 23, 25, 28 of both observation beam paths. The illustration in FIG. 2 has been significantly magnified in relation to the illustration in FIG. 1. Like in FIG. 1, generally only one of the features which are provided in pairs and, in particular, arranged symmetrically has been provided with a reference sign.

FIG. 2 indicates a housing 16 as an example of a structure which may, directly or indirectly, mechanically carry all elements, components and constituents described below and, optionally simultaneously, protect these from external influences. The housing 16 may simultaneously form the outer surface of the handling device 13 of the stereoscopic endoscope. Alternatively, the housing 16 may be provided for arrangement in a further sleeve or further housing. In this case, optical fibers for transferring illumination light or other components may be arranged between the housing 16 and the further housing.

Arranged in the handling device 13 and also within the housing 16 in the illustrated example is, near the proximal end, a control and/or signal processing device 18, which is only partly visible in FIG. 2. In particular, the control and/or signal processing device 18 is provided and embodied to supply the image sensors 60 with electrical power, control the image sensors 60, receive image signals from the image sensors 60, and amplify and prepare (e.g. digitize) the image signals.

In the example of a stereoscopic endoscope, each observation beam path comprises a relay lens system 22, which extends along the entire shaft 12 of the stereoscopic endoscope 10 (cf. FIG. 1) and the proximal end of which is visible in FIG. 2. The optical axes 23 of the relay lens systems 22 are parallel to one another and to the longitudinal axis of the stereoscopic endoscope 10, in particular the shaft 12 thereof, and lie in the sectional plane of FIG. 2.

To the proximal side of the proximal end of each relay lens system 22, provision is made of a double prism 24 with two reflecting surfaces which are parallel to one another and inclined, in particular by 45 degrees, in relation to the optical axis 23 of the relay lens system 22. The optical axes 25 within the double prisms 24 are orthogonal to the optical axes 23 of the relay lens systems 22 and likewise lie in the sectional plane of FIG. 2.

To the proximal side of each double prism 24, provision is made for an objective 26 made of a lens with positive refractive power or a plurality of lenses with, overall, positive refractive power as an optical device producing a real image. The optical axes 28 of the lenses or objectives 26 are parallel to one another and to the optical axes 23 of the relay lens systems 22 and lie in the sectional plane of FIG. 2. The double prisms 24 facilitate the optical axes 28 of the objectives 26 being spaced apart from one another significantly further than the optical axes 23 of the relay lens systems 22. The lenses or objectives 26 are, in particular, embodied and arranged in such a way that the real images generated thereby are larger or significantly larger than the cross sections of the relay lens systems 22 and the intermediate images in the relay lens systems 22.

The proximal ends of the relay lens systems 22, the double prisms 24 and the lenses or objectives 26 are arranged and held, captured or fastened in bores and/or other cavities of one or more bodies within the housing 16. A cylindrical cavity 32 is provided in a guide component 30. By way of example, the cavity 32 has a partly rectangular cross-section with, deviating from a purely rectangular cross-section, two parallel grooves 34 being provided parallel to the sectional plane of FIG. 2, to the optical axes 28 of the objectives 26 and to the longitudinal axis of the optical instrument. The edges of one of the two grooves, namely of the groove 34 lying behind the sectional plane of FIG. 2, are visible in FIG. 2. As a result of the lateral grooves 34, the cavity 32 in the guide component 30 has, overall, a substantially cross-shaped cross section with bars of different width. In the illustrated example, the guide component does not distally adjoin the adjacent body in a plane but instead extends into the adjacent body in the region of the grooves 34.

Two carriages 40 are arranged in the cavity 32 in the guide component 30. Each carriage 40 is substantially plate-shaped and extends primarily in the direction parallel to the grooves 34 and hence also to the optical axes 28 of the lenses or objectives 26 on the one hand and orthogonal to the sectional plane of FIG. 2 on the other hand. Each carriage 40 has two straight and parallel edge portions 43, which (measured in a direction parallel to the sectional plane of FIG. 2 and orthogonal to the optical axes 28 of the objectives 26) have a greater thickness than the remaining regions of the carriage 40. One straight edge portion 43 of each carriage 40 is in each case arranged or held in each groove 34 in the guide component 30.

The carriages 40 abut one another in an areal manner or, for example, only in the regions of the straight edge portions 43 thereof. The edge portions 43 of the carriages 40 and the grooves 34 in the guide component 30 and, in particular, the cross sections (in planes orthogonal to the sectional plane of FIG. 2 and to the optical axes 28 of the objectives 26) of the edge portions 43 and of the grooves 34 are embodied in such a way that the carriages 40 are guided with little play and little friction in the grooves 34 in the guide component 30. Therefore, the carriages 40 are movable or displaceable only in the direction parallel to the grooves 34 in the guide component 30 and hence parallel to the longitudinal direction of the optical instrument and parallel to the optical axes 28 of the objectives 26 and are neither swivelable or rotatable about any axis or translationally movable in any other direction.

Each carriage 40 has a used surface 45 between the two parallel straight edge portions 43 thereof. The used surfaces 45 are areal or substantially areal in each case. The used surfaces 45 of the carriages 40 face away from one another and are parallel to one another.

In one of the two parallel straight edge portions 43, each carriage 40 has a continuous bore which is at least partly provided with a female thread and parallel to the straight edge portion 43, with a set screw 48 being arranged in said bore. In FIG. 2, only the distal end of the setscrew 48 is visible in one of the two carriages 40, said end resting on a surface of the distal end of the groove 34 in the guide component 30. By rotating the setscrew 48 in the clockwise direction, the associated carriage 40 may be moved in the proximal direction. The carriage 40 may be moved in the distal direction by a force acting in the distal direction and, at the same time, by rotating the setscrew 48 in the counterclockwise direction.

A printed circuit board or circuit board 50 is arranged on the used surface 45 of each carriage 40. Each printed circuit board 50 has electrically conductive conductor tracks in, or on, an electrically insulating material. Each printed circuit board 50 has a region 54 fastened to the used surface 45 of a carriage 40. The region 54 of the printed circuit board 50 may be rigid or flexible and, in particular, it is connected in a mechanically rigid manner to the carriage 40 by way of a whole-area adhesive connection, or in another way. Each printed circuit board 50 further has a flexible and curved region 58, the proximal end of which is mechanically and electrically connected to the control and/or signal processing device 18.

An image sensor 60 is arranged on the side of each printed circuit board 50 facing away from the carriage 40. By way of example, the image sensors 60 are CCD or CMOS sensors. Each image sensor 60 has a light-sensitive layer or surface 62 which, in particular, is formed by a rectangular array or a matrix-shaped arrangement of pixels or small individually readable light-sensitive surfaces. Below, the surface of the image sensor 60 facing away from the printed circuit board 50 is, for example, referred to as light-sensitive surface 62. Electrical signals produced by the image sensor 60 are transferred to the printed circuit board 50 by way of soldering contacts, or in another way, may be amplified, or processed in another way, by electronic components (not depicted in FIG. 2) on, or in, the printed circuit board 50 and may finally be transferred to the control and/or signal processing device 18 by the flexible and curved region 58 of the printed circuit board 50.

A prism 64 made of one or more materials transparent to the light to be captured is arranged in each case on the light-sensitive surface 62 of each image sensor 60. In particular, the prism 64 is directly adhesively bonded onto the associated image sensor 60 in each case and may thus also protect the light-sensitive surface 62 of the image sensor 60. A reflecting surface 66 is provided in each prism 64. The reflecting surfaces 66 are each inclined by 45° in relation to the optical axis 28 of the objective 26 and in relation to the light-sensitive surface 62 of the image sensor 60. In particular, the reflecting surfaces 66 are formed by interfaces, at which total-internal reflection occurs, between materials with different refractive indices. Alternatively, the reflecting surface 66 of the prisms 64 could be formed by metal layers or other reflecting layers or stacks of layers.

In FIG. 2, full straight lines emanating from the edges of the objectives 26 indicate the edges of light beams which emanate from a single object point. FIG. 2 indicates that these light beams converge differently in the two optical channels downstream of the objectives 26. Therefore, the real images produced by the relay lens systems 22 and the objectives 26 are situated at different distances from the light exit surfaces of the objectives 26. This may be caused by variation of the optical properties of the employed optical elements and/or by non-ideal positioning of the optical elements.

The movability or displaceability of the carriages 40 together with the image sensors 60 and the prisms 64 facilitates an adjustment or compensation of non-ideal and non-identical properties of both beam paths. Each carriage 40 may be individually moved to the proximal direction by rotating the setscrew 48 thereof in the clockwise direction (as seen from the proximal direction) and each carriage 40 may be moved in the distal direction by rotating the setscrew 48 thereof in the counterclockwise direction and by simultaneously producing a force which pushes the carriage 40 in the distal direction. The conversion of the rotational movement into a translational movement of the setscrew 48 and of the carriage 40 by the meshing threads on the setscrew 48 and the carriage 40 facilitates a very precise adjustment of the position of each carriage 40. The connection of the image sensors 60 to the control and/or signal processing device 18 by way of the flexible and curved regions 58 of the printed circuit boards 50 in this case readily facilitates a reliable electrical connection in each position of the image sensor 60 for the purposes of transferring electrical supply power and electrical image signals.

The arrangement of the image sensors 60, more precisely of the light-sensitive surfaces 62 thereof, parallel to the direction of the optical axes 28 of the objectives 26, and hence parallel to the direction in which the two carriages 40 are movable, facilitates a particularly compact configuration of the carriages 40. The substantially plate-shaped design of the carriages 40 is producible in a comparatively simple and precise manner. The arrangement of the printed circuit boards 50 parallel to the longitudinal axis of the optical instrument, likewise emerging from this arrangement of the image sensors 60, further reduces the required installation space in comparison with an arrangement in which the printed circuit boards 50 must already be kinked or curved in the direct vicinity of the image sensors 60.

Figure 3:
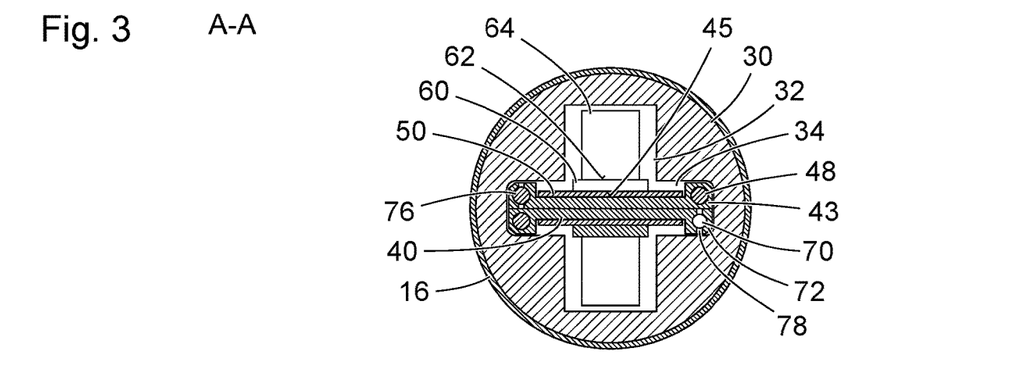
FIG. 3 shows a further schematic sectional illustration of the stereoscopic endoscope from FIG. 2.

FIG. 3 shows a further schematic sectional illustration of the handling device 13 illustrated on the basis of FIG. 2. The sectional plane A-A of FIG. 3 is orthogonal to the sectional plane of FIG. 2, to the optical axes 28 of the objectives 26, and hence also orthogonal to the direction in which the carriages 40 are movable. The position of the sectional plane A-A of FIG. 3 is indicated in FIG. 2.

The substantially cross-shaped cross section of the cavity 32 in the guide component 30 is visible in FIG. 3. Furthermore, it is possible to see how two straight edge portions 43 of the carriages 40, namely respectively one straight edge portion 43 of each carriage 40, fill the cross section of a groove 34 together in each case in such a way that, together, they are guided therein with little play and little friction. Furthermore, it is possible to see that the carriages 40 each have a significantly smaller thickness in the region of the used surfaces 45 thereof between the straight edge portions 43 than at the straight edge portions 43. In the depicted example, the carriages 40 abut against one another in an areal manner. Alternatively, the carriages 40 may abut against one another only in one or more narrow regions, for example only in two strip-shaped regions near the straight edge portions 43.

The above-described setscrews 48 for moving the carriages 40 are arranged in the right-hand straight edge portion 43 in the carriage 40 depicted at the top in FIG. 3 and in the left-hand edge portion 43 in the carriage 40 depicted at the bottom. A bore 70 and a slit 72 cutting the bore 70 in the longitudinal direction are in each case provided in the respectively opposite straight edge portions. Female threads, into which the headless screws 76 are inserted, are provided in the bores 70. However, the sectional plane A-A of FIG. 3 is arranged distally from the headless screw in the carriage 40 depicted at the bottom in FIG. 3, and so only the headless screw 76 in the bore 70 in the carriage 40 depicted at the top in FIG. 3 is visible in section in FIG. 3.

The bores 70 taper in the distal direction, i.e. the cross sections thereof reduce in the distal direction. By screwing the headless screws 76 into the tapering portions of the bores 70, the slits 72 may be widened against the elastic forces of the material of the carriage 40 and hence the carriages 40 may be locked in the guide component 30 by clamping.

Figure 4:
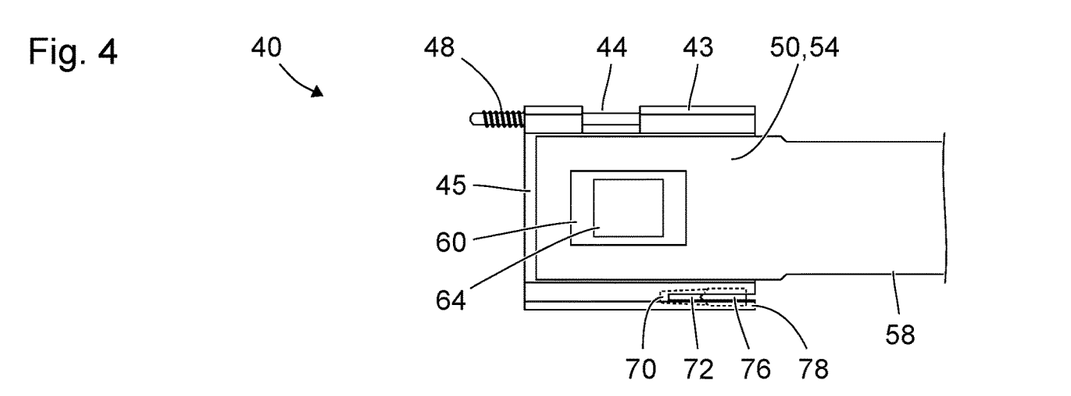
FIG. 4 shows a schematic illustration of components of the stereoscopic endoscope from FIGS. 2 and 3.

FIG. 4 shows a schematic illustration of one of the two carriages 40 from FIGS. 2 and 3. The plane of the drawing of FIG. 4 is orthogonal to the sectional plane of FIG. 2 and orthogonal to the sectional plane A-A in FIG. 3.

The recess 44 in the straight edge portion 43 of the carriage 40 is visible in the top view of FIG. 4. The setscrew 48 is visible in the recess 44. In the illustrated example, the setscrew 48 only has a thread 48 near the distal end thereof. Accordingly, the bore receiving the setscrew 48 in the straight edge portion 43 depicted at the top in FIG. 4 only has a female thread distally of the recess 44. By way of example, at the proximal end of the setscrew 48, which is not visible in FIG. 4, provision is made for a straight slit or a hexagon socket or insert bit, which facilitates an interlocking transfer of the torque from a screwdriver or another suitable tool onto the setscrew 48.

The aforementioned slit 72 and, in the slit 72, part of the headless screw 76 are visible on the opposite straight edge portion 43 of the carriage 40. The invisible contours of the headless screw 76 and of the distally tapering bore 70 are indicated using dashed lines. A tongue 78 separated from the remainder of the carriage 40 by the slit 72 may be spread by penetration of the headless screw 76 into the distally tapering bore 70 and may be pressed against the inner wall of the groove 34 (cf. FIGS. 2 and 3) in order to lock the carriage 40 in a force-fit or frictional manner.

Figure 5:
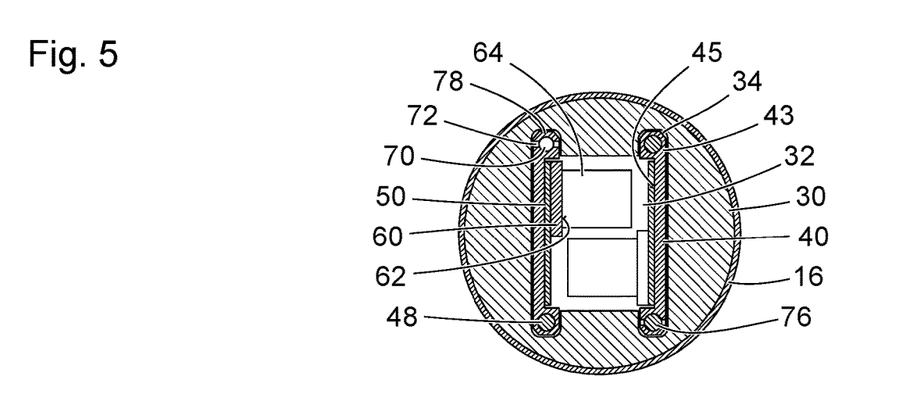
FIG. 5 shows a schematic sectional illustration of a further optical instrument.

FIG. 5 shows a schematic sectional illustration of a further optical instrument which is similar in terms of some features, properties and functions to the optical instruments depicted on the basis of FIGS. 1 to 3. The type of illustration, in particular the sectional plane, corresponds to that of FIG. 3.

The example shown in FIG. 5 differs from the example depicted on the basis of FIGS. 2 and 3 in that, in particular, two carriages 40 do not abut against one another in an areal manner but are arranged at a distance from one another in such a way that the used surfaces 45 thereof, and the printed circuit boards 50 and image sensors 60 arranged on the used surfaces 45, face one another. The image sensors 60 and prisms 64 arranged thereon are not arranged centrally, as indicated in FIGS. 3 and 4, but in each case near an edge of the associated printed circuit board 50.

The cavity 32 in the guide component 30 does not have a cross-shaped but substantially H-shaped cross section. A dedicated groove 34 is provided for each straight edge portion 43 of each carriage 40. As illustrated on the basis of FIGS. 2 to 4, each carriage 40 may be moved along a predetermined path orthogonal to the plane of the drawing in FIG. 5 by means of a setscrew 48 and may be locked by clamping by means of a headless screw 76.

Figure 6:
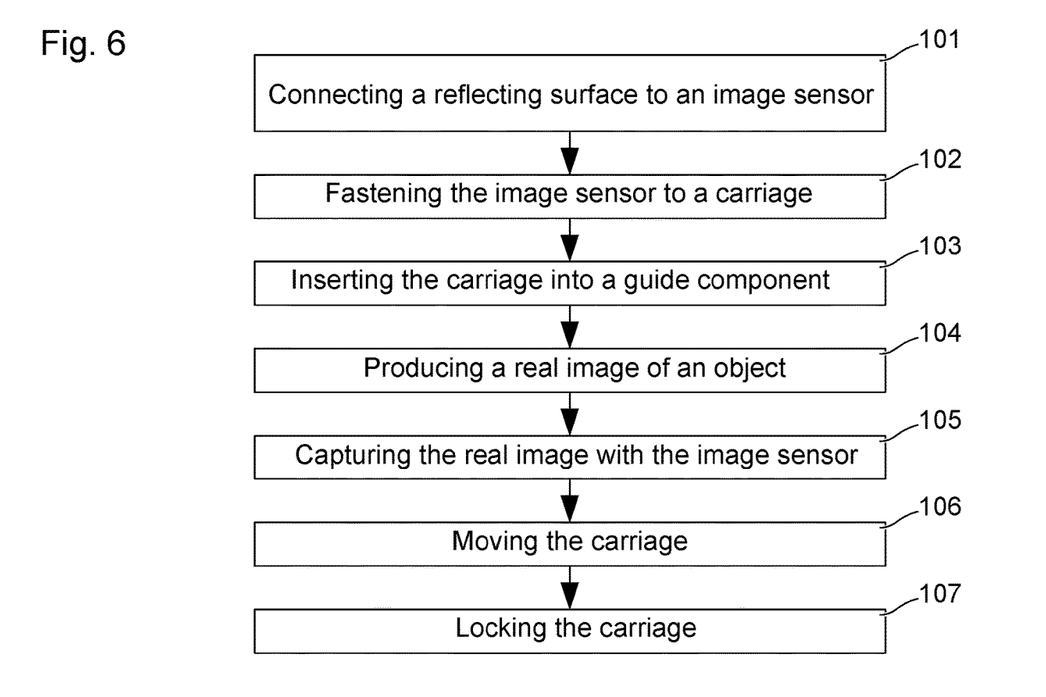
FIG. 6 shows a schematic flow chart.

FIG. 6 shows a schematic flow chart of part of a method for producing an optical instrument, in particular a stereoscopic endoscope. The method is also applicable to optical instruments with features and properties which differ from those depicted on the basis of FIGS. 1 to 5. Nevertheless, reference signs from FIGS. 1 to 5 are used below in an exemplary manner to assist with the understanding.

A reflecting surface 66 is rigidly connected to an image sensor 60 in a first step 101. In particular, the reflecting surface 66 is arranged on, or in, a prism 64, the light exit surface of which is connected, in particular directly, to a light entry surface of the image sensor 60 by means of a transparent adhesive in the first step 101.

In the second step 102, the image sensor 60 is fastened directly or indirectly (for example by way of a printed circuit board 50 disposed therebetween) to a carriage 40. The image sensor 60 or a printed circuit board 50, to which the image sensor is fastened, is connected, in particular in an areal manner, to a used surface 45 of the carriage 40 by adhesive bonding. Here, in particular, the used surface 45 of the carriage 40 and the light-sensitive surface 62 of the image sensor are, in particular, parallel to the direction in which the carriage 40 is movable.

Alternatively, the first step 101 and the second step may be carried out in the reverse order.

The carriage 40 is inserted into a guide component 30 in a third step 103. Here, in particular, two parallel straight edge portions 43 are inserted into two grooves 34, lying opposite to one another, in the guide component 30. In the third step 103, two units made of a carriage 40 and an image sensor 60 in each case, manufactured in accordance with the first step 101 and the second step 102, may be inserted into the guide component 30 simultaneously or in succession.

A real image of an object situated at a predetermined position is produced by means of an optical device in a fourth step 104. In particular, the optical device comprises an objective 26 and, optionally, a relay lens system 22. In a fifth step 105, the real image produced in the fourth step 104 is captured by means of an image sensor 60. In a sixth step 106, the carriage 40 is moved or displaced until the image sensor 60 captures the real image in focus.

The fourth step 104, the fifth step 105 and the sixth step 106 may be carried out simultaneously. The fourth step 104, the fifth step 105 and the sixth step 106 form a method for adjusting the image sensor 60, in which aberrations of the optical devices 22, 26 producing the real image may be corrected.

In a seventh step 107, the carriage 40 is locked, in particular by clamping, in the position in which the image sensor 60 captures the real image in focus.

The invention claimed is:

1. A method for adjusting an image sensor disposed in a housing of an optical instrument, comprising the following steps:

producing an image of an object arranged at a predetermined position using an optical lens disposed in the housing;

moving a carriage with the image sensor to a position within the housing in which the image sensor captures the image in focus; and locking the carriage with the image sensor at the position within the housing in which the image sensor captures the image in focus;

wherein in the moving step the image sensor is moved within the housing relative to the optical lens and in a direction parallel to a longitudinal axis extending between a proximal end and a distal end of the optical instrument.

2. An optical instrument for capturing stereo images, comprising:

a housing;

a first optical lens in the housing;

a second optical lens in the housing;

a first carriage in the housing at a proximal end of the optical instrument and moveable within the housing relative to the first optical lens and in a direction parallel to a longitudinal axis extending between a proximal end and a distal end of the optical instrument;

a second carriage in the housing at the proximal end of the optical instrument and moveable within the housing relative to the second optical lens and in a direction parallel to the longitudinal axis;

a first image sensor fastened to the first carriage and having a first light-sensitive surface configured to capture a first real image received from the first optical lens;

a second image sensor fastened to the second carriage and having a second light-sensitive surface configured to capture a second real image received from the second optical lens;

a first reflective surface in a first beam path between the first optical lens and the first image sensor; and a second reflective surface in a second beam path between the second optical lens and the second image sensor.

3. The optical instrument of claim 2, wherein the first reflective surface is rigidly connected to and moveable with the first image sensor, and the second reflective surface is rigidly connected to and moveable with the second image sensor.

4. The optical instrument of claim 2, wherein the first light-sensitive surface of the first image sensor is planar and the first carriage is movable within the housing in a direction parallel to a first plane defined by the first light-sensitive surface; and wherein the second light-sensitive surface of the second image sensor is planar and the second carriage is movable within the housing in a direction parallel to a second plane defined by the second light-sensitive surface.

5. The optical instrument of claim 2, wherein the first light-sensitive surface of the first image sensor is planar and defines a first plane parallel to the optical axis of the first optical lens; and wherein the second light-sensitive surface of the second image sensor is planar and defines a second plane parallel to the optical axis of the second optical lens.

6. The optical instrument of claim 2, further comprising a first clamp configured to lock the first carriage in a force-fit manner, and a second clamp configured to lock the second carriage in a force-fit manner.

7. The optical instrument of claim 2, further comprising a setscrew; and wherein at least one of the first carriage and the second carriage is moveable by the setscrew.

8. The optical instrument of claim 2, further comprising a printed circuit board connected to the first carriage;

wherein the first image sensor is fastened to the printed circuit board; and wherein the printed circuit board has a flexible curved portion which facilitates a length compensation when moving the first carriage.

9. The optical instrument of claim 2, wherein the optical instrument is an endoscope with a rigid shaft.

10. The optical instrument of claim 2, wherein the first optical lens is at least one lens of a first rod lens system, and the second optical lens is at least one lens of a second rod lens system.

11. The optical instrument of claim 2, wherein the first optical lens is at least one lens of a first relay lens system, and the second optical lens is at least one lens of a second relay lens system.

12. The optical instrument of claim 2, further comprising a guide rigidly connected to the first optical lens and the second optical lens, the guide having a first groove and a second groove facing away from the first groove;

wherein first and second parallel straight edge portions of the first carriage are guided in the first and second grooves, respectively.

13. The optical instrument of claim 12, wherein respectively one edge portion from each one of the two carriages is arranged, one next to the other, in each one of the two grooves.

14. The optical instrument of claim 2, wherein the two image sensors are arranged on sides facing away from one another of the two carriages.

15. The optical instrument of claim 2, wherein the first carriage is moveable relative to the housing only in the direction parallel to the longitudinal axis; and wherein the second carriage is moveable relative to the housing only in the direction parallel to the longitudinal axis.

16. The optical instrument of claim 2, wherein the first optical lens and the second optical lens are positionally fixed relative to the housing.

17. The optical instrument of claim 2, wherein the housing forms an outer surface of the optical instrument.

18. The optical instrument of claim 2, further comprising a handle and a shaft extending from the handle;

wherein the housing forms an outer surface of the handle.

19. The optical instrument of claim 2, further comprising a flexible printed circuit board connecting the first image sensor to a signal processing device.

20. The optical instrument of claim 2, further comprising a guide having at least one groove;

wherein the first carriage is guided in the at least one groove during movement within the housing.

* * * * *